United States Patent
Domingues et al.

(10) Patent No.: US 6,685,932 B1
(45) Date of Patent: Feb. 3, 2004

(54) COILED-COIL DIMER DERIVED ANTAGONISTS OF 4-HELIX BUNDLE CYTOKINES, DESIGN AND USES THEREOF

(75) Inventors: Helena Domingues, Heidelberg (DE); David Cregut, Strasbourg (FR); Walter Sebald, Würzburg (DE); Hartmut Oschkinat, Berlin-Zehlendorf (DE); Luis Serrano, Heidelberg (DE)

(73) Assignee: Europaisches Laboratorium Molekularbiologie, Heidelberg (DE)

( * ) Notice: Subject to any disclaimer, the term of this patent is extended or adjusted under 35 U.S.C. 154(b) by 0 days.

(21) Appl. No.: 09/570,337

(22) Filed: May 12, 2000

Related U.S. Application Data

(63) Continuation of application No. PCT/EP98/07286, filed on Nov. 13, 1998.

(30) Foreign Application Priority Data

Nov. 13, 1997 (EP) .............................................. 97119893
May 20, 1998 (EP) .............................................. 98109223

(51) Int. Cl.⁷ .............................................. A61K 38/20
(52) U.S. Cl. .............................. 424/85.2; 514/2; 514/8; 514/826; 514/885; 514/12
(58) Field of Search ......................... 424/85.2; 530/300, 530/327, 350; 514/2, 4, 885, 826

(56) References Cited

FOREIGN PATENT DOCUMENTS

| DE | 44 23 131 | 1/1996 |
| WO | 94 29332 | 12/1994 |

OTHER PUBLICATIONS

Grunewald et al., "An Antagonistic IL–4 M utant Prevents Type I Allergy in the Mouse: Inhibition . . . ", Journal of Immunology, vol. 160, No. 8, Apr. 15, 1998, pp. 4004–4009.

Wang et al., "A mixed–charge pair in hum an interleuk in 4 dominates high–affinity interaction with the receptor alpha chain", Pro Ceedings of the National Academy of Science of USA, vol. 94, No. 5, Mar. 4, 1997, pp. 1657–1662.

*Primary Examiner*—Prema Mertz
(74) *Attorney, Agent, or Firm*—Rothwell, Figg, Ernst & Manbeck

(57) ABSTRACT

The design of antagonists of 4-helix bundle cytokine specific receptors, mimetic peptides that are able to act as such antagonists and their use as pharmaceutical agents is disclosed.

4 Claims, 4 Drawing Sheets

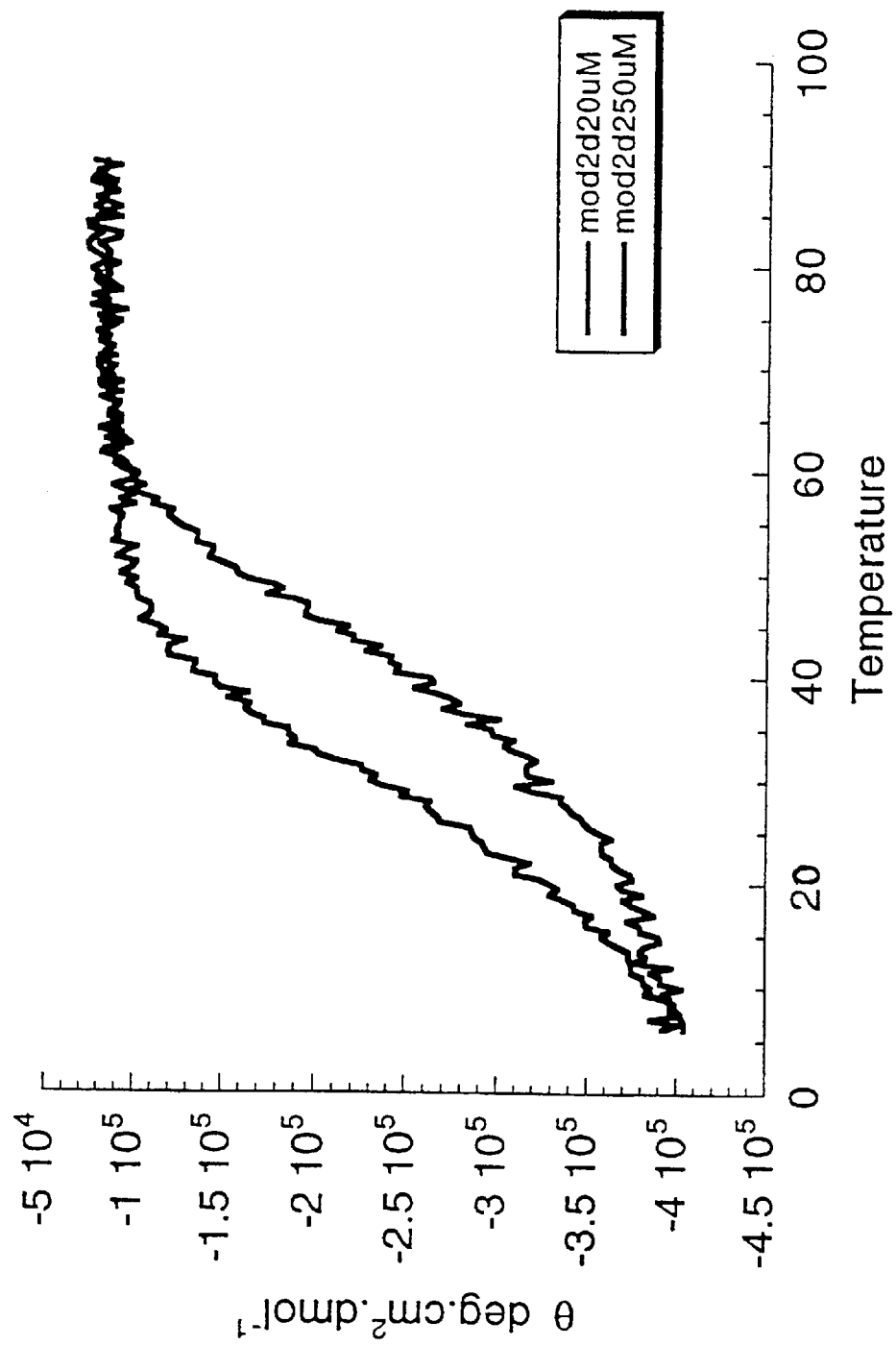
Fig. 1 Temperature induced denaturation of MAR-IL4

Fig. 2a MAR-IL4
Noesy tm = 160 ms pH 6.5
H2O 500 MHz
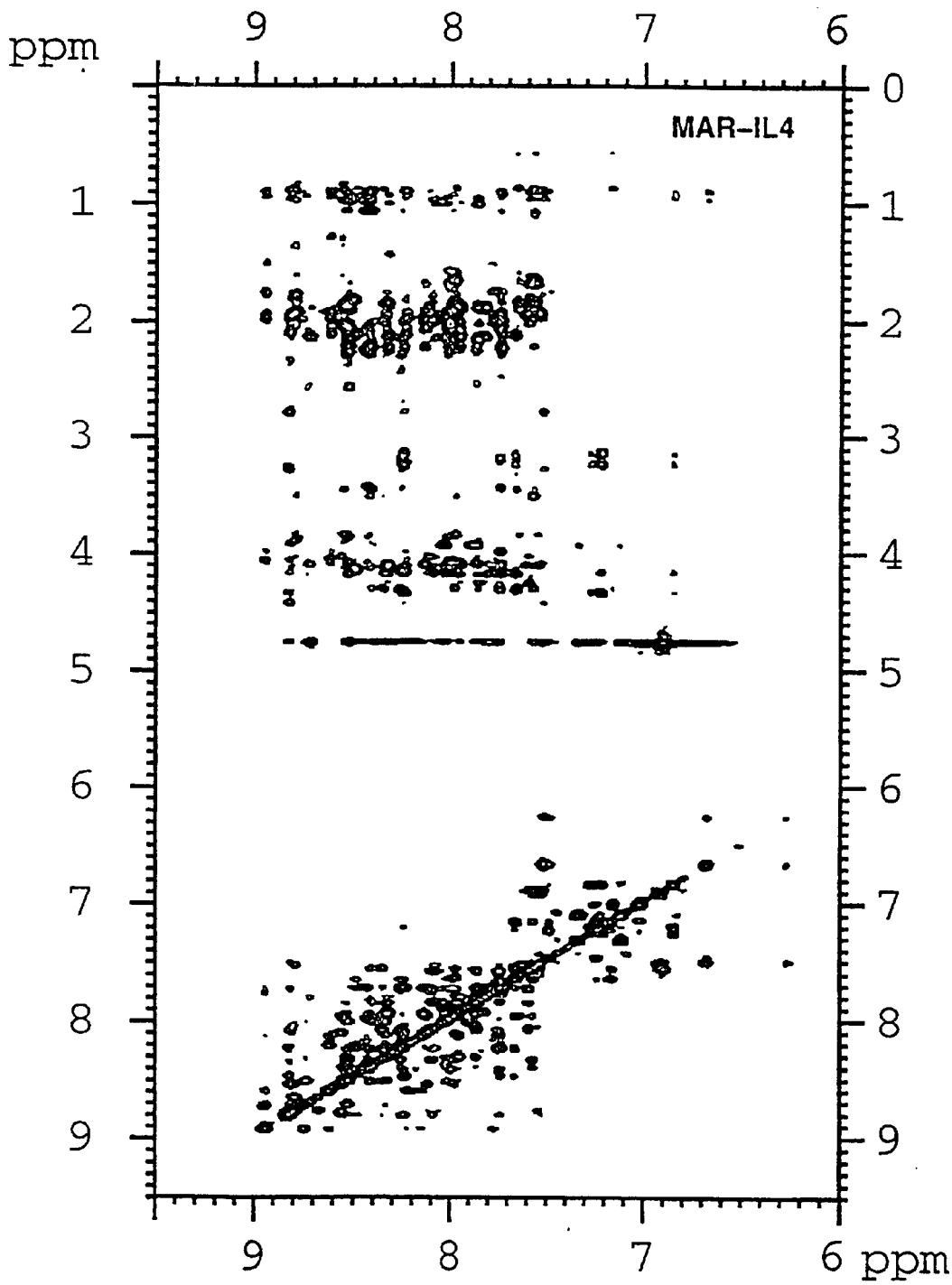

Fig. 2b GCN4 Noesy tm = 150 ms
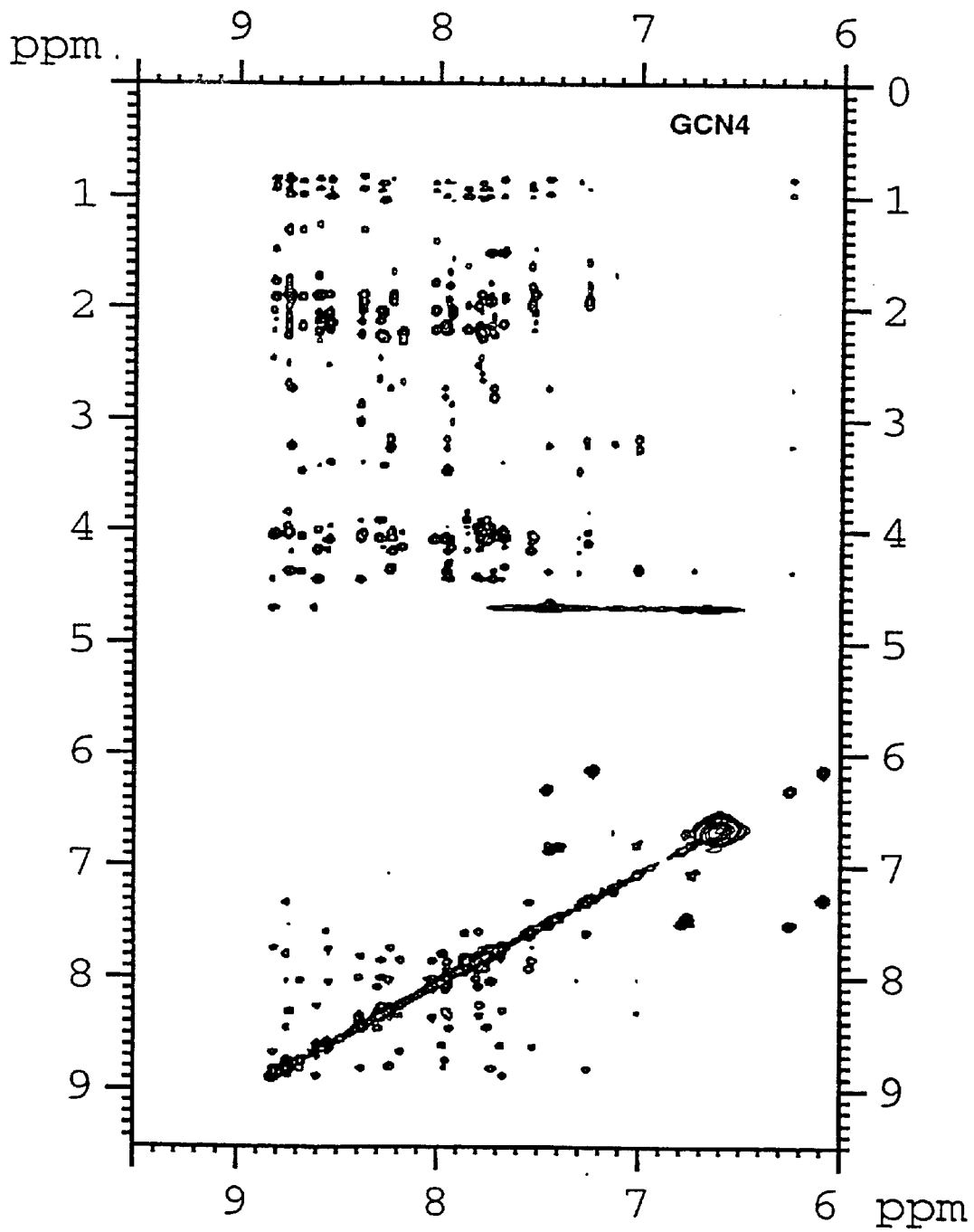

COILED-COIL DIMER DERIVED ANTAGONISTS OF 4-HELIX BUNDLE CYTOKINES, DESIGN AND USES THEREOF

CROSS REFERENCE TO RELATED APPLICATIONS

This application is a continuation of International application PCT/EP98/07286, filed Nov. 13, 1998, and designating the U.S.

BACKGROUND OF THE INVENTION

1. Field of the Invention

This invention is concerned with the design of antagonists of the interleukin-4 (IL-4) specific receptor, mimetic peptides that are able to act as such antagonists and their use as pharmaceutical agents for the treatment of disorders that are at least partly induced or mediated by the action of interleukin-4, especially the binding of interleukin-4 to its receptor.

2. Description of Related Art

Interleukin-4 is a 15 KDa glycoprotein produced mainly by T helper lymphocytes type 2 (TH2) and to a lesser extent by basophils, mast cells and eosinophils. Interleukin4 binds to the IL-4 receptor at the surface of target cells forming a binary complex that then recruits the interleukin-2 (IL-2) receptor $\gamma_c$ chain, which is also part of several other cytokine receptor systems (1–4). Upon binding to this receptor system, IL-4 can elicit different responses depending on the type of target cell, and is therefore part of the so-called pleiotropic cytokine family (5, 6). IL-4 can activate genes involved in the proliferation of T-cells, thymocytes, fibroblasts and capillary endothelial cells (7–9). It has also been reported to regulate the morphology and cytoskeletal organisation of human vascular endothelial cells, and to induce the expression of 15-lipoxygenase in monocytes (10, 11). IL-4 can also promote macrophage development by stimulating the lineage restriction of bipotent Granulocyte-Macrophage colony forming cells (12). Another important action of IL-4 is the induction of CD8+cytotoxic T-cells (13). It has also been shown that tumors cells expressing IL4 are rejected in vivo by recruited host granulocytes and macrophages (14, 15). It influences as well B-cell growth and controls IgG class switching of B cells expressing IgM into two isotypes: IgG4 and IgE (16, 17). The message conveyed to the nucleus by IL-4 upon binding to the heterodimeric receptor can lead to the expression of cell surface proteins including the IgE low affinity receptor (CD23) and the MHCII (major histocompatibility complex II) (18, 19). Transgenic mice overexpressing IL-4 present symptoms typical of allergic disease states, providing direct evidence for the pathophysiological role of IL-4 (20). It seems therefore evident that IL-4 itself, or IL-4 antagonists, may have a wide range of therapeutic applications, ranging from the treatment of allergic diseases to cancer therapy.

Allergic diseases afflict considerable parts of the population of developed countries and account for a good deal of expenses with public health services. Only a precise understanding of the cellular and molecular interactions at the basis of allergic responses will render these processes amenable to pharmaceutical control.

The allergic response developed by an individual will depend on the allergen and on the part of the body in which the allergen engages with the immune system. Allergic rhinitis is characterized by sneezing and strong congestion of the upper airways, while asthma arises in the aftermath of the obstruction and constriction of the bronchi. Perturbations of the gastrointestinal tract may also arise when the immune activity affects the contraction of smooth muscle: that surround the stomach and intestine walls (21).

When an allergen enters the body it is confronted with antigen presenting cells that are able to recognise its foreign nature, phagocytoze and degrade it. The resulting fragments are then presented to T-lymphocytes, mainly T helper lymphocytes type II (TH2). These cells secrete several cytokines, including IL-2, IL-6, IL-10, IL-13 and IL4. The response induced by IL-4 upon binding to its heterodimeric receptor complex involves an intrachromosomal rearrangement event that leads to immunoglobulin class switching of B plasma cells from IgM to IgG4 and IgE. IL-4 is also able to upregulate the expression of the IgE low affinity receptor (CD23) on mast cells and B cells and the expression of its own receptor on lymphocytes. The allergen-specific immunoglobulin E antibodies associate with their receptor on the surface of mast cells in tissue and on basophils circulating in blood. When an allergen binds to two IgE molecules it will bring together their receptors, which results in the activation of different signal transduction pathways involving several enzymatic systems. This culminates with the secretion of a plethora of molecules by mast cells including histamine, cytokines and lipid moleculesilike prostaglandins and leukotrines. These are indeed the agents responsible for the allergic symptoms. As more IL-4 is produced by mast cells, this perpetuates its presence at the site of inflammation, causing an explosive reaction which in some instances can lead to hypotensive shock and even death. Hypotensive shock is characterized by a drop in blood pressure accompanied by a dramatic reduction in the supply of oxygen to the heart and brain, that arise as a consequence of widespread vascular changes induced by histamine (21–23).

In view of what has been stated above it seems clear that IL-4 is a dominant cytokine in allergic inflammation, for it determines whether B-cells give rise to IgE or other types of antibodies. Consequently, drugs capable of interfering with the activity of IL-4 will help reduce IgE levels and therefore control allergic reactions.

The activity of IL-4 can be inhibited by preventing the interaction of IL-4 with its receptor system, thereby suppressing the intracellular signals that are at the basis of allergic disease. The strategies available up to date to block cytokine-receptor interactions involve the use of monclonal antibodies against a cytokine or its receptor, soluble receptors and cytokine receptor antagonists (24, 25). Receptor antagonists are proteins that are capable of binding cytokine receptors with high affinity but are incapable of inducing signal transduction and therefore do not generate a biological response. Often receptor antagonists can be generated by mutating the wild-type cytokine. In this way, cytokine-derived antagonists have been successfully obtained for IL-4, growth hormone, prolactin and IL-6 (26–29). For interleukin-1 a natural receptor antagonist has been reported and recently the crystal structure of this antagonist complexed with the interleukin-1 receptor has been determined (30, 31). Nevertheless, thus far no other natural cytokine receptor antagonists are known.

The therapeutic potential of soluble receptors and monoclonal antibodies has been shown to be rather limited. Soluble receptors bind cytokine ligands with lower affinity than their membrane bound counterparts and therefore, in order to achieve efficient inhibition of the cytokine response, intolerable levels of soluble receptors would have to be applied. Furthermore, antibody or soluble receptor-cytokine complexes tend to be cleared off the body at much slower rate than the ligand alone. These complexes will then accumulate in the circulation and constitute a depot form of the cytokine that can be released later on. Because of the high turnover rate of protein molecules in the human body repeated administration would be required, rendering the treatment expensive and often dangerous because of possible immunogenicity of these proteins (24, 25, 32). For these reasons, much hope has been given to the advent of the above mentioned cytokine-derived antagonists as efficient therapeutical molecules. This new generation of biopharmaceuticals was expected to be of lower toxicity compared to other substances (33). However, recombinant cytokines are difficult to produce in large amounts in a cost-effective way. Most of the recombinant therapeutic proteins and vaccines available on the market are produced by large-scale fermentation of *Escherichia coli* carrying a gene coding for the protein of interest. In the particular case of cytokines and growth factors, including IL-4, this production strategy is hindered by the fact that these proteins generally form inclusion bodies when overexpressed in *E. coli*. The purification of the cytokine, or cytokine derivative, from inclusion bodies requires the use of chaotropic agents like guanidinium chloride, urea or strong detergents. An in vitro renaturation step then follows during which the protein is expected to fold into its three-dimensional structure (34). Although many proteins have been reported to have been successfully refolded from inclusion bodies, in the case of cytokines the yield of correctly folded protein is usually very low (35). Therefore, in vitro renaturation processes remain inefficient and expensive and it is quite difficult to achieve a perfect separation of the properly folded protein from: certain misfolded forms. This fact poses a serious drawback to the use of these proteins for therapeutic purposes, since even small amounts of improperly folded protein can be immunogenic. But this is not the only disadvantage that places cytokine derived therapeutics in a rank far from ideal medicines. All the inconveniences associated with protein drugs, like short serum half-life due to rapid proteolysis by serum proteolytic enzymes, low oral availability, and low local effectiveness as a consequence of systemic administration, have to be added to the list (33, 36). In principle, gene therapy is expected to circumvent most of these problems by making possible the expression proteins within the body at specific sites under tight control (37). However, gene therapy technology is still in its infancy, and meanwhile alternative therapeutic solutions have to be put forward.

In recent years, advancements in structural biophysical techniques, like Nuclear Magnetic Resonance (NMR), X-ray crystallography or Electron Microscopy, have made possible the determination of protein or protein complexes three-dimensional structures at high resolution. Additionally, NMR also offers the possiblity of investigating the dynamic properties of biomacromolecules in solution (38, 39). In the last years the three-dimensional structure of several cytokines and growth factors, like IL-2, IL-4, IL-6, GM-CSF, and hGH, has been determined by X-ray crystallography or NMR (40–51). The structure of these cytokines consists of four helices connected by two long loops containing short segments of α-helix or β-sheet structure. Such an arrangement of four helices forms the so-called four-helix bundle structural motif. All the cytokines listed above display an up-up-down-down-topoloy of the helices (52).The structure of the complex of the hGH bound to its homodimeric receptor and to the prolactin receptor has also been made available (53–55). Simultaneously, a great effort has been devoted to the mapping of the putative receptor binding epitopes by site-directed mutagenesis (56, 57). The comparison of the mutagenesis and structural data is of pivotal importance to the understanding of the structure-function relationship of cytokine-receptor systems and allows the identification of crucial intermolecular interactions at the active site. The structure of the human growth hormone-receptor complex shows that despite the fact that a large surface area is buried both on the hormone and on the receptor upon binding, corresponding to approximately 33 side chains on both molecules, only 9 residues contribute significantly to the binding energy (58–60). These data suggest that functional epitopes mediating growth factor or cytokine-receptor interaction may be rather small, and therefore there is a good chance that they can be emulated by rationally designed small peptide molecules. These peptidomimetics should be able to play the role of larger polypeptide ligands in recognising and/or activating receptor targets, and would be used as or developed into potent cytokine or cytokine receptor agonist or antagonist drugs.

When it comes to the development of therapeutic peptides researchers are confronted with the challenge of finding the best possible candidate that is able to mediate the desired bilogical effect in the most efficient way. This is usually achieved by creating libraries of compounds that have diverse molecular shapes and functional characteristics. Phage display technology has been of precious help in the creation and screening of vast peptide libraries (61–63). This methodology has been successfully used to isolate peptide mimetics of erythropoietin (EPO). One of these peptides is able to bind the EPO receptor with a 0.2 μM affinity constant (Kd) and the three-dimensional structure of this peptide in complex with the EPO receptor has also been determined (64, 65). The small peptide dimerizes forming a four-stranded anti-parallel β-sheet that is able to bind two EPO receptor molecules and induce a response similar to erythropoietin. Phage display has also been used to imp rove the stability and affinity of a two-helix derivative of the three-helix Z-domain of protein A. This 59 residue three-helix bundle binds the Fc portion of Immunoglobulin G (IgG) with a Kd of 10 nM. By using a combination of phage display and structural data the binding domain has been reduced to a 33 residue peptide that is able to bind IgG with virtually the same affinity as the wild-type protein (66). The 15-residue atrial natriuretic peptide (ANP) mimetic is another example of a synthetic peptide that has been selected by phage display to specifically bind a receptor molecule (67).

The present invention relates to the rational design of an interleukin-4 mimetic peptide using methodologies herein described below.

BRIEF DESCRIPTION OF THE DRAWINGS

Figure 3:
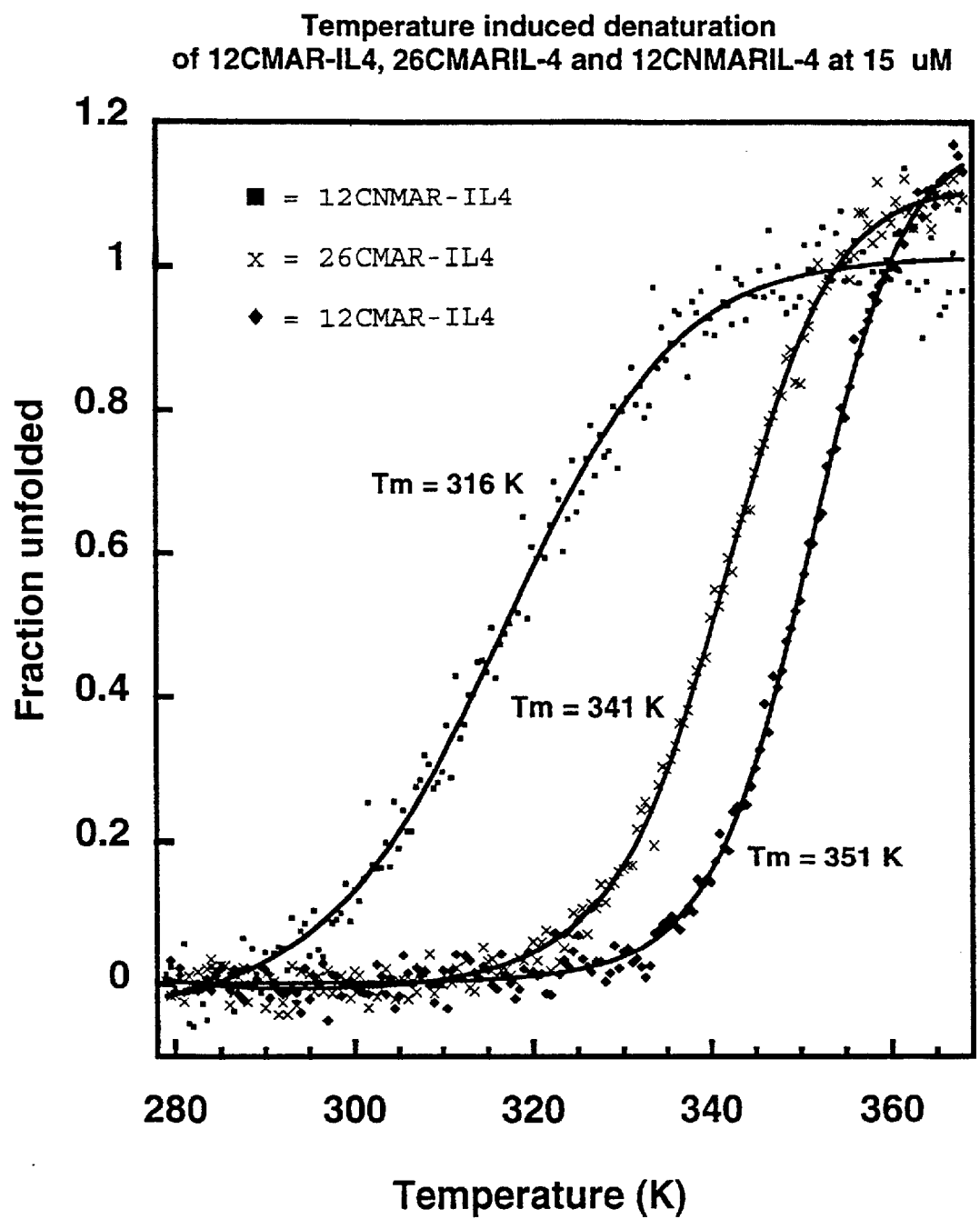

FIG. 1 shows the temperature-induced denaturation curve of MAR-IL4 at two different peptide concentrations: 20 μM and 250 μM. It is clear that MAR-IL4 exhibits a cooperative temperature induced transition characteristic of a folded protein. The midpoint of the transition is concentration dependent, being displaced to higher temperatures at higher peptide concentrations where the dimeric form of the peptide is more populated. At the low peptide concentrations used to measure the binding to IL4Rα, MAR-IL4 starts losing its structure at 25° C. and is partly unfolded at 25° C., the temperature at which the binding assays were done. Therefore, its affinity for the receptor should be significantly higher than the value that was found. In order to achieve tighter binding the stability of the peptide is improved in particular by introducing a disulfide bridge.

In FIG. 2a and 2b, parts of NOESY NMR spectra of MAR-IL4 and GCN4 are shown. The aromatic and amide regions are plotted in F1 showing the connectivities to the other protons along F2. These spectra show a pattern of signals characteristic of a protein with high helical content. It is also evident that the spectrum of MAR-IL4 closely resembles that of GCN4.

FIG. 3 shows the temperature-induced denaturation of the peptides containing a cysteine residue, followed by Circular Dichroism at 222 nm. All the transitions are very cooperative and the transition temperature of these peptides is independent of the concentration due to the formation of a disulfide bridge between the peptide monomers. Scattered symbols represent the experimental data and solid lines are the best fits to these data assuming a two state transition from the folded dimer to the unfolded monomer (Thompson, K. S., Vinson, C. R., Freire, E., (1993), Biochemistry 32, 5491–5496). Upon fitting the experimental data, the midpoint transition temperature (Tm) can be obtained.

DETAILED DESCRIPTION OF THE PREFERRED EMBODIMENTS

The invention relates to designing a peptide capable of inhibiting the activity of interleukin-4 by preventing its interaction with the specific IL-4 receptor (IL-4Rα). Interfering with the binding of IL-4 to the $\alpha_c$ chain of the heterodimeric receptor complex would be problematic, for this chain is also part of several other cytokine receptor systems, as previously stated.

Interleukin-4 has been shown by both X-ray crystallography and NMR to consist of a four-helix bundle with up-up-down-down connection and exhibit three-disulfide bridges. C3–C127 which connects the N and C-termini of the protein, C24–C65 between the AB and BC loop; C64–C99 which connects helix B to the CD loop (42–46, 48). Site directed mutagenesis data and monoclonal antibodies show that the residues involved in binding the IL-4Rα are mainly located in two of the helices: helix A and helix C (56, 68, 69). Therefore, we thought it would be possible to design a two helix peptide mimetic of IL-4 bearing the residues that had been postulated to interact with the IL-4Rα in the correct spatial orientation. The leucin-zipper domain of the yeast transcription factor GCN4 was used as a template for molecular modelling studies. This domain has been shown to form a stable parallel coiled-coil dimer in solution, and an extensive description of its structural and thermodynamic properties is available in the literature (70–78). The coiled-coil dimer is a structural motif which results from the coiling of two right-handed helices around one another with a slight left-handed twist, and is very common in many fibrous proteins and transcription factors (79). At least three nuclear transforming proteins, Jun, Fos and Myc, have been shown to contain leucine-zipper domains that, upon forming a coiled coil, mediate the homo or hetero dimerization of these proteins. The mammalian transcription regulator C/EBP is another example of a protein bearing a coiled coil motif (80–84).

The putative IL-4 epitope was transferred to the surface of the coiled coil of the GCN4 leucine zipper domain. Mutations were introduced into the primary sequence of GCN4 in such a way that the stability of the coiled-coil and its tendency to form parallel dimmers, would not be significantly altered. Using this strategy, 6 peptides were designed containing different combinations of the residues expected to contribute significantly to the binding energy at the IL-4-IL/4Rα interface. In one of the peptides, MAR IL4, all the residues that have been suggested to be involved in binding to the IL-4Rα were included. All the peptides were synthesized by solid phase methods, aminated on the C-terminus and acetylated on the N-terminus. The activity of the peptides was investigated by biosensor-based binding experiments using the BIA2000 system (Pharmacia Biosensor), at room temperature. The extracellular domain of the IL-4Rα, (so-called IL-4 binding protein -IL4BP), biotinylated at Cys-206 and immobilised at the streptavidin-coated matrix of the biosensbr was used as a receptor a chain analogue (85). Two of the peptides did not show a significant specific binding to the IL-4Rα; three of the remaining peptides exhibit a low affinity binding activity—Kd ranging from 2000 to 100 μM. The magnitude of the dissociation constant correlates with the number of residues from the hormone putative epitope included in the peptide. MAR-IL4 shows the tightest binding (Kd=26 μM). Under the same experimental conditions the affinity of the interleukin-4 for IL-4Rα was determined to be 1.4 nM. Thermodynamic and molecular dynamics studies of the above mentioned peptides reveal that at the temperature at which the activity assays were performed (–25° C.), the coiled-coil starts losing its structure showing signs of partial denaturation. This suggests that the affinity of MAR-IL4 for the interleukin-4 specific receptor can indeed be much higher than the one measured at 25° C., for at this temperature the stability of the peptides is low. These experimental data suggest that by increasing the structural stability of MAR-IL4, a peptide mimetic of IL-4 is obtained that binds to its specific receptor with a binding constant close to that of the hormone, and could therefore be used as an inhibitor of the IL-4 activity for therapeutic purposes. In order to stabilize the structure of MAR-IL4 an interhelical disulfide bridge was introduced into the coiled-coil peptide. An extensive study of the role of disulfide bridges in the stability of coiled-coil structures and proteins in general is available in the literature (86–88).

The introduction of a disulfide bridge into the sequence of MAR-IL4, either at position 12 or 26, leads to the formation of very stable covalent dimers upon oxidation of the peptide monomers (see Example 2). A 5-fold increase in the binding affinity to IL-4Rα is observed as a consequence of this increase in stability. In order to further optimize the binding of the disulfide linked MAR-IL4 to the IL-4 receptor, an asparagine residue was introduced at position 19 and a leucine residue at position 16. This asparagine residue has been found to play a very important role in the binding of IL-4 to its specific receptor (68). The observed decrease in stability was expected since the mutation was introduced into the core of the coiled coil. However, the binding affinity for IL-4Rα remained exactly the same as that of the original disulfide bound MAR-IL4 peptide (5 μM). This experimental evidence strongly argues in favor of this residue being very important for the activity of the peptide, and suggests that by improving the stability of this peptide, its affinity to the IL-4 receptor is thereby increased. A capping box and a hydrophobic staple motif were introduced at the N-terminus of the peptide sequence, and a Schellman motif at the C-terminus. These motifs are very often found at the beginning and at the end of helices in the protein data base and have been reported to contribute significantly to the stability of these elements of secondary structure (89–91).

This is the first time a high affinity cytokine receptor antagonist has been successfully obtained solely based on computer-assisted molecular modelling methods, without resorting to phage display technology. This is also the first IL-4 receptor antagonist peptide discovered until now. Most cytokines share the same common four-helix bundle structural motif displaying binding epitopes located at least partially in two of the four helices (52, 92, 93). Therefore, the approach described above may also be applied to other cytokine receptor systems in an attempt to design novel cytokine receptor agonist or antagonist molecules.

By preserving the spatial geometric relationship of the functionally important residues in IL-4, the Inventors have been able to transform a peptide unrelated in sequence or function to interleukin-4, into a peptidomimetic that is able to recognise and bind specifically the IL-4 receptor with an affinity close to that of the hormone. MAR-IL4 or a MAR-IL 4-derivative can be developed into a potent therapeutic drug that, when sprayed into the lungs, is able to alleviate allergic symptoms like those associated with the production of mucus and intensive congestion of the airways.

Peptide based therapeutics offer several advantages compared to protein derived drugs. Peptide entities are less complex than the protein molecules they are meant to emulate. This chemical and structural simplicity makes their large-scale production either by genetic engineering techniques or by solid phase methods straightforward. Besides allowing the production of large quantities of product, genetic engineering techniques also offer a means of producing easily mutant peptide sequences. These mutants can be used to test the role of different amino acid residues in the function and stability of the designed peptide. Fusion expression systems in which the gene encoding the molecule of interest is fused to a tag through a sequence containing a protease cleavage site are usually the most convenient choice for the expression of small proteins or peptide molecules in $E.\ coli$ or yeast (94–98). The c-Fos and c-Jun leucine zipper peptides and several of their derivative mutants, have already been successfully overexpressed in heterologous hosts (99, 100). The fact that these peptides are of a size similar to that of the peptides described in this work and that they share the same coiled coil leucine zipper motif strongly suggests that the latter may also be successfully obtained by genetic engineering techniques. Nevertheless, the fact that unnatural aminoacid derivatives like D-amino acids or small chemical functional groups cannot be incorporated into peptide sequences overexpressed in prokaryotic or eukaryotic expression systems constitutes a main stumbling block to the routine use of genetic engineering methods for therapeutic peptide production. These unnatural chemical moieties that may render the peptides intrinsically more stable or less susceptible to proteolytic degradation in the body, can be readily introduced by solid phase peptide synthesis methods. The possibility of incorporating a wide variety of natural and non-natural compounds into the sequence of the peptide also constitutes a precious tool in the development of small nonpeptide drug molecules that are able to provide the distinct functional groups needed for molecular interactions and bioactivity while offering much better biostability and oral bioavailability (101–104). The IL-4 mimetic peptide of the invention, MAR-IL4, will allow these strategies to be explored. Hence, there is hope that an optimal therapeutic drug capable of antagonising the activity of interleukin-4 in an efficient and specific way may one day be achieved.

Therefore, an object of this invention was to provide a possibility to prevent interaction of 4-helix bundle cytokines to their specific receptors and especially of IL-4 and its specific receptor IL-4Rα.

This problem is solved by a mimetic peptide described herein, its production and its use as a pharmaceutical agent for preventing physiological disorders that are induced or mediated by the binding of 4-helix bundle cytokines and especially IL-4 to its receptor(s).

A preferred peptide mimics binding of an 4-helix bundle cytokine to its receptor but does not induce the effects that binding of the cytokine to the receptor does, containing parts of the cytokine that interact with the receptor, or derivatives thereof, introduced into the primary sequence of a coiled-coil dimer in such a way that the. stability of the coiled coil and its tendency to form paralleled dimers are not significantly altered.

It is also possible to improve the affinity of the peptide system according to this invention, especially by introducing a disulfide bridge, but also by mutating other residues in GCN4 that are not directly involved in the binding region. Also, the introduction of non-natural amino acids prolongs the life of the compound in vivo. Finally, this approach could be used for other interleukin molecules which are also folded as 4-helix bundles.

The experimental data provided below show that MAR-IL4 is folded in solution, and binds IL-4Rα with an affinity that could allow its use as an antagonist of IL4.

EXAMPLE 1

The experimental data provided in this section show that MAR-IL4 is folded in solution and binds IL-4Rα with an affinity close to that of interleukin4 (cf. FIGS. 1 and 2).

The design of IL-4Rα was done following a hierarchic approach in which 6 peptides containing different combinations of the IL-4 residues expected to contribute significantly to the binding energy at the IL4-IL-4Rα interface were designed. MAR-IL4 (SEQ ID NO: 6) contains all the residues that have been suggested to be involved in the binding to IL-4Rα. This peptide shows the highest affinity for IL-4Rα, as can be seen from the below table.

TABLE I

| Peptide | Sequence (SEQ ID NO:) | Kd iM |
| --- | --- | --- |
| Model 1 | RMKQLEDKVEELLSKNYRLENRVARLEKLVG (1) | 105597 |
| Model 2 | RMKQLEDKVERLLSRNYRLENEVARLKKLVG (2) | 4082 |
| Model 2a | RMKQLEKKVERLLKRNYRLENEVARLKKLVG (3) | 2160 |
| Model 2b | RMKQLEKKVERLLKRNYRLENEVIRLKKLVG (4) | 193 |
| Model 2c | RMKQLEKKVERLLKRNYRLEWEVARLKKLVG (5) | 106 |
| MAR-IL-4 | RMKQLEKKVERLLKRNYRLEWEVIRLKKLVG (6) | 26 |
| IL-4 |  | 1.4 nM |

EXAMPLE 2

Design of a GCN4 derived antagonist of the interleukin-4 (IL-4) specific receptor (IL-4Rα)

The experimental data provided in this section prove that upon introducing a cysteine residue into the primary sequence of MAR-IL4, a 5-fold increase in the binding affinity is achieved (SEQ ID NO: 7). This increase in affinity is correlated with the increase in stability which occurs upon oxidation of the cysteine-containing peptides and formation of covalent dimers. The disulfide linked. dimers were purified by RP-HPLC and their molecular weight confirmed by mass spectrometry. They exhibit a midpoint transition temperature much higher than that of MAR-IL-4.

Introduction of a leucine at position 16 and an asparagine residue at position 19 into the sequence of the peptide bearing a cysteine at position 12 (SEQ ID NO: 9), leads to a significant drop in the stability of the peptide although the binding affinity is not affected. The asparagine residue is equivalent to asparagine 89 in IL-4 which contributes significantly to the binding to IL-4Rα. Our results strongly suggest that asparagine 19 is critical for the binding activity of the peptide and that by improving the stability of this peptide we will also improve its affinity for the IL-4 receptor. These investigations ar now being made.

The sequences of the peptides containing a cysteine residue as well as those of the peptides mentioned in Example 1 are shown in Table II along with their binding affinities.

The design of the IL-4Rα antagonist peptides was done following a hierarchic approach in which 6 peptides containing different combinations of the IL-4 residues expected to contribute significantly to the binding energy at the IL-4-IL/4Rα interface were designed. From these peptides, MAR-IL4 showed the highest affinity for IL-4Rα. Further optimization of the sequence of this peptide by the introduction of a cysteine residue and other residues which form part of the IL-4 binding epitope, lead to a 5-fold increase in the binding affinity.

TABLE II

| Peptide | Sequence (SEQ ID NO:) | Kd iM |
|---|---|---|
| Model 1 | RMKQLEDKVEELLSKNYRLENRVARLEKLVG (1) | 105597 |
| Model 2 | RMKQLEDKVERLLSRNYRLENEVARLKKLVG (2) | 4082 |
| Model 2a | RMKQLEKKVERLLKRNYRLENEVARLKKLVG (3) | 2160 |
| Model 2b | RMKQLEKKVERLLKRNYRLENEVIRLKKLVG (4) | 193 |
| Model 2c | RMKQLEKKVERLLKRNYRLEWEVARLKKLVG (5) | 106 |
| MAR-IL-4 | RMKQLEKKVERLLKRNYRLEWEVIRLKKLVG (6) | 26 |
| IL-4 | | 1.4 nM |
| 12CMAR-IL4 | RMKQLEKKVERCLKRNYRLEWEVIRLKKLVG (7) | 5 |
| 26CMAR-IL4 | RMKQLEKKVERLLKRNYRLEWEVIRCKKLVG (8) | 5–10 |
| 12CNMAR-IL4 | RMKQLEKKVERCLKRLYRNEWEVIRLKKLVG (9) | 5 |

References

1. Hoffmann, R. C., Castner, B. J., Gerhart, M., Gibson, M. J., Rasmussen, B. D., March, C. J., Weatherbee, J., Tsang, M., Gutschina, A., Schalk-Hihi, C., Reshetnikova , L., Wlodaver, A. (1995), Direct evidence of a heterotrimeric complex of human interleukin-4 with its receptors, Protein Science 4, 382–386.
2. Boulay, J.-L., Paul, W. A. (1992), The interleukin-4 related lymphokines and their binding to hematopoietin receptors, J. Biol. Chem. 267, 20525–20528.
3. Bazan, J. F. (1990), Structural design and molecular evolution of a cytokine receptor superfamily, Proc. Natl. Acad. Sci. USA 87, 6934–6938.
4. Ihle, J. N., Witthuhn, B. A., Quelle, F. W., Yamamoto, K., Silvennoinen, O. (1995), Signalling through the hematopoietic cytokine receptors, Ann. Rev. Immunol. 13, 369–398.
5. Lian, J.-X., Migone, T.-S., Tsang, M., Friedman, M., Weatherbee, J. A., Yamamauchi, L. A., Bloom, E. T., Mietz, J., John, S., Leonard, W. J. (1 995), The role of shared receptor motifs and common stat proteins in the generation of cytokine pleiotropy and redundancy by IL-2, IL-4, IL-7, IL-13 and IL-15, Immunity 2, 331–339.
6. Paul, W. E., Seder, R. A. (1994), Lymphocyte responses and cytokines, Cell 76, 241–251.
7. Toi, M., Harris, A. L., Bicknell, R. (1991), IL-4 is a potent mitogen for capillary endothelium, Biochem. Biophys. Res. Commun. 174, 1287–1293.
8. Barcena, A., Sanchez, M. J., Dela Pompa, J. L., Toribio, M. L., Kroemer, G., Marinez, A. C. (1991), Involvement of the. interleukin-4 pathway in the generation of functional gamma, delta T cells from human pro T-cells, Proc. Natl. Acad. Sci. USA 88, 7689–7693.
9. Defrance, T., Vanvesliet, B., Anbry, J. P., Takebe, Y., Arai, N., Miyajima, A., Yokota, T., Lee, F., Arai, K. I., de Vries, J. E., Bancherau, J. (1 987), B-cell growth promoting activity of recombinant interleukin-4.
10. Conrad, D. J., Kuhn, H., Mulkins, M., Highland, E., Sigal, E. (1992), Specific inflammatory cytokines regulate the expression of human monocytelS-lipoxygenase, Proc. Natl. Acad. Sci USA 89, 217–221.
11. Schleimer, R. P., Sterbinsky, S. A., Kaiser, J., Bicket, C. A., Klunk, D. A., Tomioka, K., Newman, W., Luscinskas, F. W., Gimbrone, M. A., Jr., McIntyre, B. W., Bochner, B. S. (1992), IL-4 induces adherence of human eosinophils and basophils but not neutrophils to endothelium, J. Immunol. 198, 1086–1092.
12. Nichols, S. E., Heyworth, C. M., Dexter, M. T., Lord, J. M., Johnson, G. D., Whetton, A. D. (1995), IL-4 promotes macrophage development by rapidly stimulating lineage restriction of bipotent granulocyte colony forming cells, J. Immunol. 155, 845–853.
13. Dullens, H. F. D., C. L. (1991), Cancer treatment with interleukins 1, 4 and 6 and combination of cytokines: a review, In Vivo 5, 567–570.
14. Tepper, R. I., Coffman, R. L., Leder, P. (1992), An eosinophil-dependent mechanism for the antitumor effect of interleukin-4, Science 257, 548–551.
15. Tepper, R. I., Pattengale, P. K., Leder, P. (1989), Murine IL-4 displays potent anti-tumor activity in vivo, Cell 57, 503–512.
16. De Vries, J. E., Carballido, J. M., Sornasse, T., Yssel, H. (1995), Antagonizing the differentiation and functions of human T helper type 2 cells, Current Opinion in Immunology 7, 771–778.
17. De Vries, J. E., Gauchet, J. F., Aversa, G. G., Punnonen, J., Gascan, H., Yssel, H. (1991), Regulation of IgE synthesis by cytokines, Curr. Opin. Immunol. 3, 851–858.
18. Daser, A., Meissner, N., Herz, U., Renz, H. (1995), Role and modulation of T-cell cytokines in allergy, Current Opinion in Immunology 7, 762–770.
19. Conrad, D. H., Waldschmidt, T., Lee, W. T., Rao, M., Keegan, A. D., Noelle, R. J., Lynch, R. G., Kehry, M. R.

(1987), Effect of B-cell stimulatory factor-I (interleukin 4) on Fce and Fcg receptor expression on murine B lymphocytes and B cell lines, J. Immunol. 139, 2290–2296.
20. Tepper, R. L., Levinson, D. A., Stanger, B. Z., Campos-Torres, J., Abbas, A. K., Leder, P. (1990), IL-4 induces allergic-like inflammatory disease and alters T cell development, Cell 62, 457–467.
21. Allergy: principles and practice (1988), in Middleton, E., Jr., Reed, C. E., Ellis, E. F., Adkinson, N. F., Yunginger, J. W., Mosby, C. V. (eds.).
22. Lichtenstein, L. M. (1993), Allergy and the immune system, Scientific American 269, 85–93.
23. Asthma: physiology, immunopharmacology and treatment (1984), in: Kay, A. B., Austen, K. F. and Lichtenstein, L. M. (eds.), Academic Press.
24. Brunt, J. V. (1989), Lymphokine receptors as therapeutics, Biotechnology 7, 668–669.
25. Rettig, M. (1997), Interleukin-6: an antagonizing problem becomes a solution, Nature Biotechnology 15, 952–953.
26. Kruse, N., Tony, H.-P., Sebald, W. (1992), Conversion of human IL-4 into a high affinity antagonist by a single amino acid replacement, EMBO Journal 11, 3237–3244.
27. Fuh, G., Cunningham, B. C., Fukunaga, R., Nagata, S., Goeddel, D. V., Wells, J. A. (1992), Rational design of potent antagonists to the human growth hormone receptor, Science 256, 1677–1680.
28. Brakenhoff, J. P. J., de Hon, F. D., Fontaine, V., ten Boekel, E., Schooltink, H., Rose-John, S., Heinrich, P. C., Content, J., Aarden, L. A. (1 994), Development of a human IL-6 receptor antagonist, J. Biol. Chem. 269, 86–93.
29. Fuh, G., Colosi, P., Wood, W. I., Wells, J. A. (1993), Mechanism-based design of prolactin receptor antagonists, J. of Biological Chemistry 268,5376–5381.
30. Schreuder, H., Tardif, C., Trump-Kallmeyer, S., Soffientini, A., Sarubi, E., Akeson, A., Bowlins, T., Yanofsky, Barrett, R. W. (1997), A new cytokine receptor binding mode revealed by the crystal structure of the IL-1 receptor with an antagonist, Nature.
31. Vigers, G. P. A., Anderson, L. J., Caffes, P., Brandhuber, B. J. (1997), Crystal structure of the type-1 interleukin-1 receptor complexed with interleukin-1â, Nature 386, 190–194.
32. Rose-John, S., Heinrich, P. C. (1994), Soluble receptors for cytokines and growth factors: generation and biological function, Biochem. J. 300, 281–290.
33. Buckel, P. (1996), Recombinant proteins for therapy, Trends in Protein Science 17, 450–456.
34. Van Kimmenade, B. M. W., Schumacher, J. H., Laquoi, C., Kaistelein, R. A. (1998), Expression, renaturation and purification of recombinant interleukin-4 from *Escherichia coli*, Eur. J. Biochem. 173, 109–114.
35. Hockney,. R. C. (1994), Recent developments in heterologous protein production in the *Escherichia coli*, Trends in Biotechnology 12, 456–463.
36. Konrad, M. (1989), immunogenicity of proteins administered to humans for therapeutic purposes, Trends in Biotechnology 7, 175–178.
37. Anderson, W. F. (1992), Human gene therapy, Science 256, 808–813.
38. Brünger, A. (1997), X-ray crystallography and NMR reveal complementary views of structure and dynamics, Nature Structural Biology 4, 862–865.
39. Wagner, G. (1997), An account of NMR in structural biology, Nature Structural Biology 4, 841–844.
40. Brandhuber, B. J., Boone, T., Kenney, W. C., McKay, D. B. (1987), Three-dimensional structure of interleukin-2, Science 238, 1707–1709.
41. Bazan, F. (1992), Unraveling the structure of IL-2, Science 257, 410–414.
42. Powers, R., Garrett, D. S., March, C. J., Frieden, E. A., Gronenborn, A. M., Clore, G. M. (1993), The high resolution three-dimensional structure of human interleukin-4 determined by multidimensional heteronuclear magnetic resonance spectroscopy, Biochemistry 32, 674–6762.
43. Redfield, C., Smith, L. J., Boyd, J., Lawrence, G. M. P., Edwards, R. G., Gershater, C. J., Smith, R. A. G., Dobson, C. M. (1994), Analysis of the solution structure of human interleukin-4 determined by heteronuclear three-dimensional nuclear magnetic resonance techniques, J.Mol. Biol. 238, 23–41.
44. Redfield, C., Smith, L. J., Boyd, J., Lawrence, G. M. P., Edwards, R. G., Smith, R. A. G., Dobson, C. M. (1991), Secondary structure and topology of human interleukin-4 in solution, Biochemistry 30, 11029–11035.
45. Smith, L. J., Redfield, C., Boyd, J., Lawrence, J. M., Edwards, R. G., Smith, R. A., Dobson, C. M. (1992), Human interleukin-4: the solution structure of a four-helix bundle protein, J. Mol. Biol. 224, 899–904.
46. Smith, L. J., Redfiled, C., Smith, R. A. G., Dobson, C. M., Clore, G. M., Gronenborn, A., Walter, M. R., Naganbushan, T. L., Wlodaver, A. (1994), Comparison of four independently determined structures of human recombinant interleukin-4, Structural biology 1, 301–310.
47. Walter, M. R., Cook, W. J., Zhao, B. G., Cameron, R. P., Ealick, S. E., Jr., Water, R. L., Reichert, P., Jr., Nagabhushan, T. L., Trotta, P. P., Bugg, C. E. (1992), Crystal structure of human interleukin-4, J. Biol. Chem. 267, 20371–20376.
48. Wlodaver, A., Pavlovsky, A., Gustchina, A. (1992), Crystal structure of human recombiriant interleukin-4 at 2.25 A resolution, FEBS 309, 59–64.
49. Xu, G.-Y., Yu-Ha, Hong, J., Stahl, M., McDonagh, T., Kay, L. E., Cumming, D. A. (1997), Solution structure of recombinant human interleukin-6, J. Mol. Biol. 268, 468–481.
50. Walter, M. R., Cook, W. J., Ealick, S. E., Nagabhushan, T. L., Trotta, P. P., Bugg, C. E. (1992), Three-dimensional structure of recombinant human granulocyte-macrophage colony-stimulating factor, J. Mol. Biol. 224.
51. Ultsch, M., Somers, W., Kossiakoff, A. A., de Vos, A. M. (1994), The crystal structure of affinity-matured human growth hormone at 2 Å resolution, J. Mol. Biol. 236, 286–299.
52. Wlodaver, A., Pavlovsky, A., Gustchina, A. (1993), Hematopoietic cytokines: similarities and differences in structures with implications for receptor binding, Protein Science 2, 1373–1382.
53. De Vos, A. M., Ultsch, M., Kossiakoff, A. A. (1992), Human growth hormone and extracellular domain of its receptor: crystal structure of the complex, Science 2S5, 306–312.
54. Kossiakoff, A. A. et al. (1994), Comparison of the intermediate complexes of human growth hormone bound to the human growth hormone and prolactin receptors, Protein Science 3, 1697–1705.
55. Somers, W., Ultsch, M., de Vos, A. M., Kossiakoff, A. A. (1994), The x-ray structure of a growth hormone-prolactin receptor complex, Nature 372, 478–481.
56. Müller, T., Dieckmann, T., Sebald, W., Oschkinat, H. (1994), Aspects of receptor binding site and signalling of interleukin-4 investigated by site-directed mutagenesis and NMR spectroscopy, J. Mol. Biol. 237, 423–436.
57. Cunningham, B., Wells, J. A. (1989), High resolution epitope mapping of the hGH-receptor interactions by alanine-scanning mutagenesis, Science 244, 1082–1086.

58. Cunningham, B. C., Wells, J. (1993), Comparison of a structural and functional epitope, J. Mol. Biol. 234, 554–563.
59. Wells, J. A. (1 996), Binding in the growth hormone receptor complex, Proc. Natl. Acad. Sci USA 93, 1–6.
60. Clackson, T., Wells, J. A. (1995), A hot spot of binding energy in a hormone-receptor interface, Science 267, 383–386.
61. Cwirla, S. E., Peters, E. A., Barrett, R. W., Dower, D. J. (1990), Peptides on phage: a vast library of peptides for identifying ligands, Proc. Natl. Acad. Sci. USA 87, 6387–6382.
62. Scott, J., Smith, G. P. (1990), Searching for peptide ligands with an epitope library, Science 386–390.
63. Smith, G. (1985), Filamentous fusinon phage: novel expression vectors that display cloned antigens on the virion suface, Science 1315–1317.
64. Wrighton, N. C., Farrell, F. X., Chang, R., Kashyap, A. K., Barbone, F. P., Mulcahy, L. S., Johnson, D. L., Barrett, R. W., Jolliffe, L. K., Dower, W. J. (1996), Small peptides as potent mimetics of the protein hormone eritropoietin, Science 273, 458–463.
65. Livnah, 0., Stura, E. A., Johnson, D. L., Middleton, S. A., Mulcahy, L. S., Wrighton, N. C., Dover, W. J., Jollife, L. K., Wilson, I. A. (1996), Functional mimicry of a protein hormone by a peptide agonist: the EPO receptor complex at 2.8 A, Science 273, 464–471.
66. Braisted, A. C., Wells, J. (1996), Minimizing a binding domain from protein A, Proc. Natl. Acad. Sci. USA 93, 5688–5692.
67. Cunningham, B. C. L. D., Li, B., Bennett, B. D., Wells, J. A. (1994), Production of an atrial natriuretic peptide variant that is specific for type A receptor, EMBO J. 13, 2508–2515.
68. Wang, Y., Shen, B. J., Sebald, W. (1997), A mixed-charged pair in human interleukin-4 dominates high-affinity interaction with the receptor a chain, Proc. Natl. Acad. Sci. USA 94, 1657–1662.
69. Reusch, P., Arnold, S., Heusser, C., Wagner, K., Weston, B., Sebald, W. (1994), Neutralizing monoclonal antibodies define two different functional sites in human interleukin-4, Eur. J. Biochem. 222, 491–499.
70. O'Shea, E. K., Klemm, J. D., Kim, P. S., Alber, T. (1991), X-ray structure of the GCN4 leucihe zipper, a two-stranded, parallel coiled coil, Science 25, 539–544.
71. Saudek, V., Pastore, A., Morelli, M. A. C., Frank, R., Gausephol, H., Gibson, T. (1991), The solution structure of a leucine-zipper peptide, Protein Engineering 4, 519–529.
72. Kenar, K. T., Garcia-Moreno, B., Freire, E. (1995), A calorimetric characterization of the salt dependence of the stability of the GCN4 leucin zipper, Protein Science 4, 1934–1938.
73. Thompson, K. S., Vinson, C. R., Freire, E. (1993), Thermodynamic characterization of the structural stability of the coiled-coil region of the bZIP transcription factor GCN4, Biochemistry 32, 5491–5496.
74. Harbury, P. B., Zhang, T., Kim, P. S., Alber, T. (1993), A switch between two-, three- and four-stranded coiled coils in GCN4 leucine zipper mutants, Science 262, 1401–1407.
75. Harbury, P. B., Kim, P. S., Alber, T. (1994), Crystal structure of a leucine-zipper trimer, Nature 371, 80–83.
76. Zhou, N. E., Kay, C. M., Hodges, R. S. (1992), Synthetic model proteins: the relative contributions of leucine residues at the nonequivalent positions of the 3–4 hydrophobic repeat to the stability of the two-stranded alpha helical coiled-coil, Biochemistry 31, 5739–5746.
77. Zhou, N. E., Kay, C. M., Hodges, R. S. (1992), Synthetic model proteins: positional effects of interchain hydrophobic interactions on stability of two-stranded alpha-helical coiled-coils, J. Biol. Chem. 267, 2664–2670.
78. Zhou, N. E., Zhu, B.-Y., Kay, C. M., Hodges, R. S. (1992), The two-stranded alpha helical coiled-coil is an ideal model for studying protein stability and subunit interactions, Biopolymers 32, 419–426.
79. O'Shea, E. K., Rutkowski, R., Kim, P. S. (1988), Evidence that the leucine zipper is a coiled coil, Science 243, 538–543.
80. Landschlutz, W. H., Johnson, P. F., McKnight, S. L. (1988), The leucine-zipper: a hypothetical structure common to a new class of DNA binding proteins, Science 240, 1759–1764.
81. Gentz, R., Rauscher III, F. J., Abate, C., Curran, T. (1989), Parallel association of Fos and Jun leucine zippers juxtaposes DNA binding domains, Science 243, 1695–1699.
82. O'Shea, E. K., Rutkowski, R., Stafford III, W. F., Kim, P. S. (1989), Preferential heterodimer formation by isolated leucine zippers from Fos and Jun, Science 245, 646–648.
83. Turner, R., Tjan, R. (1989), Leucine repeats and adjacent DNA binding mediate the formation of functional c-Fos-c-Jun heterodimers, Science 1989, 1689–1694.
84. Vinson, C. R., Sigler, P. B., McKnight, S. L. (1989), Scissors-grip model for DNA recognition by a family of leucine zipper proteins, Science 246, 911–916.
85. Shen, B.-J., Hage, T., Sebald, W. (1996), Global and local determinants for the kinetics of interleukin-4/interleukin-4 receptor interaction. A biosensor study employing recombinant interleukin-4-binding protein, Eur. J. Biochem. 240, 252–261.
86. Zhou, N. E., Kay, C. M., Hodges, R. S. (1993), Disulfide bond contribution to protein stability: positional effects of substitution in the core of the two-stranded alpha-helical coiled-coil, Biochemistry 32, 3178–3187.
87. Doig, A. J., Williams, D. H. (1991), Is the hydrophobic effect stabilizing or destabilizing? The contribution of disulfide bonds to protein stability, J. Mol. Biol. 217, 389–398.
88. Myzka, D. G., Chaiken, I. M. (1994), Design and characterization of an intramolecular antiparallel: coiled coil peptide, Biochemistry 33, 2363–2372.
89. Muñoz, V., Serrano, L. (1995), Analysis of i, i+5 and i, i+8 hydrophobic interactions in a helical model peptide bearing the hydrophobic staple motif, Biochemistry 34, 15301–15306.
90. Viguera, A. R., Serrano, L. (1995), Experimental analysis of the Schellman motif, J. Mol. Biol. 251, 150–160.
91. Aurora, R., Srinivasan, R., Rose, G. D. (1994), Rules for a-helix termination by glycine, Science 264, 1126–1128.
92. Wlodaver, A., Pavlovsky, A., Gustchina, A. (1993), Hematopoietic cytokines: similarities and differences in structure with implications for receptor binding, Protein Science 2, 1373–1382.
93. Mott, H. R., Campbell, I. D. (1995), Four-helix bundle growth factors and their receptors: protein-protein interactions, Current Opinion in Structural Biology 5, 114–121.
94. Wells, J. A., de Vos, A. M. (1996), Hematopoietic receptor complexes, Annu. Rev. Biochem. 65, 609–634.
95. Smith, D. B., Johnson, K. S. (1988), Single-step purification of polypeptides expressed in *Escherichia coli* as fusions with glutathione S-transferase, Gene 67, 31–40.
96. Sharrocks, A. D. (1994), A T7 expression vector for producing N-and C-terminal fusion proteins with gluthatione S-transferase, Gene 138, 105–108.

97. Guan, K. L., Dixon, J. E. (1991), Eukaryotic proteins expressed in *Escherichia coli*: an improved thrombin cleavage and purification procedure of fusion proteins with glutathione S-transferase, Anal. Biochem. 192, 262–267.
98. Parks, T. D., Leuther, K. K., Howard, E. D., Johnston, S. A., Dougherty, W. G. (1994), Release of proteins and peptides from fusion proteins using a recombinant plant virus proteinase, Anal. Biochem. 216, 413–417.
99. Lu, Q., Bauer, J. C., Greener, A. (1997), Using schizosaccharomyces pombe as a host for expression and purification of eukaryotic proteins, Gene 200, 135–144.
100. Schuermann, M., Hunter, J. B., Henning, G., Müller, R. (1991), Non-leucine residues in the leucine repeats of Fos and Jun contribute to the stability and determine the specificity of dimerization, Nucleic Acids Res. 19, 739–746.
101. Riley, L. G., Ralston, G. B., Weiss, A. S. (1996), Multimer formation as a consequence of separate homodimerization domains: the human c-Jun leucine zipper is a transplantable dimerization module, Protein Eng. 9, 223–230.
102. Kelly, W. S. (1996), Therapeutic peptides: the devil in details, Biotechnology 14, 28–30.
103. Emmos, T.-K., Murali, R., Greene, M. (1997), Therapeutic peptides and peptidomimetics, Current Opinion in Biotechnology 8, 435–441.
104. DeGrado, W. F., Sosnick, T. (1996), Protein minimization: downsizing through mutation,: Proc. Natl. Acad. Sci. USA 93, 5680–5681.
105. Myers, A. G., Gleason,:J. L., Yoon, T. (1995), A practical method for the synthesis of D- or laininoacids by the alkylation of (+) or (−) pseudoephedrine glycinamide, J. Am. Chem. Soc. 117, 8488–8489.

What is claimed is:

1. A method of treating allergic reactions that are induced or mediated by binding of a 4-helix bundle cytokine to its specific receptor(s) in a patient in need of such treatment, comprising administering to said patient, a 4-helix bundle cytokine antagonist, wherein the antagonist comprises a 4-helix bundle cytokine receptor-binding peptide sequence within a peptide sequence for a coiled-coil dimer, with the proviso that the antagonist inhibits 4-helix bundle cytokine binding without mediating a biological response through the receptor, wherein the 4-helix bundle cytokine is IL-4, and wherein the 4-helix bundle cytokine receptor-binding protein sequence is selected from the group consisting of the amino acid sequence of SEQ ID NO:6 and a modification of the amino acid sequence of SEQ ID NO:6, wherein said modification inhibits cytokine binding without mediating a biological response through the receptor.

2. The method of claim 1, wherein said modification is selected from the group consisting of the amino acid sequence of SEQ ID NO:7, SEQ ID NO:8 and SEQ ID NO:9.

3. A pharmaceutical composition for inhibiting binding of a 4-helix bundle cytokine to its receptor, comprising a receptor-binding inhibitory effective amount of a 4-helix bundle cytokine antagonist comprising a 4-helix bundle cytokine receptor-binding peptide sequence within a peptide sequence for a coiled-coil dimer, with the proviso that the antagonist inhibits cytokine binding without mediating a biological response through the receptor, and a pharmaceutically acceptable carrier, wherein the 4-helix bundle cytokine is IL-4, and wherein the 4-helix bundle cytokine receptor-binding protein sequence is selected from the group consisting of the amino acid sequence of SEQ ID NO:6 and a modification of the amino acid sequence of SEQ ID NO:6, wherein said modification inhibits cytokine binding without mediating a biological response through the receptor.

4. The pharmaceutical composition of claim 3, wherein said modification is selected from the group consisting of the amino acid sequence of SEQ ID NO:7, SEQ ID) NO:8 and SEQ ID NO:9.

* * * * *

SEQUENCE LISTING

```
<160> NUMBER OF SEQ ID NOS: 9

<210> SEQ ID NO 1
<211> LENGTH: 31
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<223> OTHER INFORMATION: Model 1, interleukin-4 mimetic peptide 105597
      Kd micrometers

<400> SEQUENCE: 1

Arg Met Lys Gln Leu Glu Asp Lys Val Glu Glu Leu Leu Ser Lys Asn
1               5                   10                  15

Tyr Arg Leu Glu Asn Arg Val Ala Arg Leu Glu Lys Leu Val Gly
            20                  25                  30

<210> SEQ ID NO 2
<211> LENGTH: 31
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<223> OTHER INFORMATION: Model 2, interleukin-4 mimetic peptide 4082 Kd
      micrometers

<400> SEQUENCE: 2

Arg Met Lys Gln Leu Glu Asp Lys Val Glu Arg Leu Leu Ser Arg Asn
1               5                   10                  15

Tyr Arg Leu Glu Asn Glu Val Ala Arg Leu Lys Lys Leu Val Gly
            20                  25                  30

<210> SEQ ID NO 3
<211> LENGTH: 31
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<223> OTHER INFORMATION: Model 2a, interleukin-4 mimetic peptide 2160 Kd
```

-continued

```
      micrometers

<400> SEQUENCE: 3

Arg Met Lys Gln Leu Glu Lys Lys Val Glu Arg Leu Leu Lys Arg Asn
1               5                   10                  15

Tyr Arg Leu Glu Asn Glu Val Ala Arg Leu Lys Lys Leu Val Gly
            20                  25                  30

<210> SEQ ID NO 4
<211> LENGTH: 31
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<223> OTHER INFORMATION: Model 2b, interleukin-4 mimetic peptide 193 Kd
      micrometers

<400> SEQUENCE: 4

Arg Met Lys Gln Leu Glu Lys Lys Val Glu Arg Leu Leu Lys Arg Asn
1               5                   10                  15

Tyr Arg Leu Glu Asn Glu Val Ile Arg Leu Lys Lys Leu Val Gly
            20                  25                  30

<210> SEQ ID NO 5
<211> LENGTH: 31
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<223> OTHER INFORMATION: Model 2c, interleukin-4 mimetic peptide 106 Kd
      micrometers

<400> SEQUENCE: 5

Arg Met Lys Gln Leu Glu Lys Lys Val Glu Arg Leu Leu Lys Arg Asn
1               5                   10                  15

Tyr Arg Leu Glu Trp Glu Val Ala Arg Leu Lys Lys Leu Val Gly
            20                  25                  30

<210> SEQ ID NO 6
<211> LENGTH: 31
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<223> OTHER INFORMATION: MAR-IL-4, interleukin-4 mimetic peptide 26 Kd
      micrometers

<400> SEQUENCE: 6

Arg Met Lys Gln Leu Glu Lys Lys Val Glu Arg Leu Leu Lys Arg Asn
1               5                   10                  15

Tyr Arg Leu Glu Trp Glu Val Ile Arg Leu Lys Lys Leu Val Gly
            20                  25                  30

<210> SEQ ID NO 7
<211> LENGTH: 31
<212> TYPE: PRT
<213> ORGANISM: Artificial Sequence
<220> FEATURE:
```

```
<221> NAME/KEY: misc_feature
<223> OTHER INFORMATION: Description of Artificial Sequence: synthetic
      peptide
<221> NAME/KEY: misc_feature
<223> OTHER INFORMATION: 12CMAR-IL4, interleukin-4 mimetic peptide 5 Kd
      micrometers

<400> SEQUENCE: 7

Arg Met Lys Gln Leu Glu Lys Lys Val Glu Arg Cys Leu Lys Arg Asn
1               5                   10                  15

Tyr Arg Leu Glu Trp Glu Val Ile Arg Leu Lys Lys Leu Val Gly
            20                  25                  30

<210> SEQ ID NO 8
<211> LENGTH: 31
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<223> OTHER INFORMATION: 26CMAR-IL4, interleukin-4 mimetic peptide, 5-10
      Kd micrometers

<400> SEQUENCE: 8

Arg Met Lys Gln Leu Glu Lys Lys Val Glu Arg Leu Leu Lys Arg Asn
1               5                   10                  15

Tyr Arg Leu Glu Trp Glu Val Ile Arg Cys Lys Lys Leu Val Gly
            20                  25                  30

<210> SEQ ID NO 9
<211> LENGTH: 31
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<223> OTHER INFORMATION: 12CNMAR-IL4, interleukin-4 mimetic peptide 5 Kd
      micrometers

<400> SEQUENCE: 9

Arg Met Lys Gln Leu Glu Lys Lys Val Glu Arg Cys Leu Lys Arg Leu
1               5                   10                  15

Tyr Arg Asn Glu Trp Glu Val Ile Arg Leu Lys Lys Leu Val Gly
            20                  25                  30
```